(12) United States Patent
Kawamoto

(10) Patent No.: US 6,172,253 B1
(45) Date of Patent: Jan. 9, 2001

(54) PROCESS FOR RECYCLING SILICONE COMPOUNDS

(75) Inventor: Takeshi Kawamoto, Shizouka (JP)

(73) Assignee: Yazaki Corporation, Tokyo (JP)

(*) Notice: Under 35 U.S.C. 154(b), the term of this patent shall be extended for 0 days.

(21) Appl. No.: 09/456,919

(22) Filed: Dec. 7, 1999

(30) Foreign Application Priority Data

Dec. 7, 1998 (JP) .................................................. 10-346832

(51) Int. Cl.[7] ......................................................... C07F 7/08

(52) U.S. Cl. ............................................................. 556/466

(58) Field of Search .............................................. 552/466

(56) References Cited

FOREIGN PATENT DOCUMENTS

| 9-77779 | 3/1997 | (JP) . |
|---|---|---|
| 9-176364 | 7/1997 | (JP) . |

*Primary Examiner*—Paul F. Shaver
(74) *Attorney, Agent, or Firm*—Armstrong, Westerman, Hattori, McLeland & Naughton

(57) ABSTRACT

A process for recycling a silicone compound wherein the silicone compound is decomposed by employing an alkyl carbonate and a compound containing active hydrogen group in the presence of a catalyst, and silicone monomers and/or silicone oligomers are recovered from the decomposed silicone compound. Silicone monomers and/or silicone oligomers are produced without producing any byproduct, and no step for removal by separation is needed in an after process, and therefore the implementation is easy.

5 Claims, No Drawings

PROCESS FOR RECYCLING SILICONE COMPOUNDS

BACKGROUND OF THE INVENTION (1) Field of the Invention

This invention relates to a process for recycling silicone compounds.

(2) Description of the Related Art

The recycling of scrapped plastics is a global demand and a variety of resins have been tried to be recycled in response to the demand. As one of these trials, the recycling of silicone resins has been tried from many standpoints of view.

In Japanese Patent Application Laid-Open No. Heisei 9-176364, proposed was a process in which silicone resins were decomposed into monomers or oligomers, which can be recycled, by using orthocarboxylic ester compounds, compounds containing active hydrogen group, and catalysts.

The above process is good since the process can be put into practice under a relatively mild condition and at a relatively low cost. However, the process produces an unwanted byproduct through the hydrolysis of orthocarboxylic ester, for example, methyl formate when methyl orthoformate is used as the orthocarboxylic ester. Since monomers or oligomers containing the orthocarboxylic ester can not be used as they are, the separation of orthocarboxylic ester (for example, Japanese Patent Application Laid-Open No. Heisei 9-7779) has been needed in an after process. Therefore, the above process has not been practical and resulted in an obstruction to the implementation on an industrial scale.

SUMMARY OF THE INVENTION

It is therefore an object of the present invention to provide a process for recycling silicone compounds, solving the above-mentioned problem, in which silicone monomers and/or silicone oligomers are produced without producing any byproducts, and no treatment for removing orthocarboxylic ester by separation is needed in the after process, and therefore the implementation of the present invention is easy and practical.

In order to achieve the object, according to a first aspect of the present invention, there is provided a process for recycling silicone compounds comprising the steps of: decomposing the silicone compound by employing an alkyl carbonate and a compound containing active hydrogen group in the presence of a catalyst; and recovering silicone monomers and/ or silicone oligomers from the decomposed silicone compound.

According to a second aspect of the present invention, there is provided a process wherein the catalyst is preferably an acid catalyst.

According to a third aspect of the present invention, there is provided a process wherein the alkyl carbonate to employ is preferably a dimethyl carbonate.

According to a fourth aspect of the present invention, there is provided a process wherein the catalyst is preferably an acid catalyst and also the alkyl carbonate is preferably a dimethyl carbonate.

According to a fifth aspect of the present invention, there is provided a process wherein the compound containing active hydrogen group is preferably an alcohol.

According to the process for recycling silicone compounds of the present invention, many silicone compounds can be easily recycled. Furthermore, as for the process, the conditions are mild, the recycling cost is not expensive because the reagents used are comparatively cheap, and the safety is high. The process is superior to the prior-art process because silicone compounds, which have at least one hydrogen atom or more as substituents bonded to silicon atoms, can be decomposed and recycled without causing any damages to Si-H bonds, and no treatment for removal of orthocarboxylic ester by separation is needed.

DESCRIPTION OF THE PREFERRED EMBODIMENTS

According to the present invention for recycling silicone compounds, either a vapor phase process or a liquid phase process can be implemented for the decomposition reaction of the silicone compound.

In the present invention, the silicone compound, which is subjected to the recycling, is a compound having siloxane bonds (Si—O—Si bonds) in the molecule regardless of the molecular weight. The compound may be a mixture with other organic or inorganic compounds, and a copolymer of a silicone compound with other compounds. Any morphology for the silicone compound, such as vapor, liquid, paste, and solid phase, is applicable.

In the present invention, the silicone compound which is subjected to the recycling is, for example, such as silicone oil, silicone grease, silicone oil compounds, silicone oil secondary products, silicone rubber, silicone rubber compounds, silicone rubber processed goods, liquid silicone rubber, silicone sealant, silicone elastomer, silicone resin, silicone varnish, silane coupler having siloxane bonds (Si—O—Si bonds) in the molecule, and copolymer of silicone with organic polymer. However, the silicone compounds are not limited to the examples described above. Many of these silicone compounds are on the market as commercial products or intermediates.

In the present invention, the recycling process may be applied to a single silicone compound or may be applied to a plurality of silicone compounds in combination. The compound may be cured or uncured in any morphology such as vapor, liquid, and solid. Among the silicone compounds which are subjected to the recycling according to the present invention, the recycle of straight chain polysiloxane is easy and the recycle of straight chain polysiloxane, which have hydrogen atoms as substituents bonded to silicon atoms, is particularly easy.

The alkyl carbonate, which is a reactant for decomposing the silicone compound in accordance with the present invention, is for example such as dimethyl carbonate and diethyl carbonate, although the alkyl carbonate is not limited to these examples. The single alkyl carbonate may be used, or a plurality of alkyl carbonates may be used in combination. Among the alkyl carbonates, a diethyl carbonate is preferable, since by the hydrolysis a diethyl carbonate produces methanol which is a highly reactive compound containing active hydrogen group.

The amount of use of alkyl carbonate is not particularly limited, but is preferably equal molar amount to that of the water generated by the decomposition of the silicone compound, or is more preferably more than that.

The compound containing active hydrogen group of the present invention, which is a reactant for decomposing the silicone compound, is a compound containing, for example, such as hydroxyl group, carboxyl group, mercapto group, formyl group and amino group, or a compound which generates a compound containing such as hydroxyl group, carboxyl group, mercapto group, formyl group and amino group in the molecule as a result of reaction with an orthocarboxylic ester compound. To give an actual example, the compound is such as water, alcohol, carboxylic acid, thiol and amine, although the compound is not limited to these examples. Among these compounds, water and/or alcohol is preferable from the viewpoint of high reaction rate. The compound, which is contained in the starting material or in the reaction system as an impurity, also contributes as the compound containing active hydrogen group, for example, such as water and/or alcohol. Methanol is preferable as the compound containing active hydrogen group from the viewpoint of high reaction rate.

The single compound containing active hydrogen group may be used, or a plurality of compounds containing active hydrogen group may be used in combination. When the compound containing active hydrogen group is not used, the reaction neither occur nor proceed significantly, and the yield of the recycle becomes extremely low because the reaction rate of the silicone compound becomes low and the silicone compound is not decomposed perfectly.

The catalyst, which is used for the decomposition reaction of silicone compounds in the present invention, is such as hydrochloric acid, sulfuric acid, fuming sulfuric acid, nitric acid or acetic acid, for example, although the catalyst is not limited to these examples. The single catalyst may be used, or a plurality of catalyst may be used in combination. The catalyst is preferably an acid catalyst from the viewpoint of reactivity, and is more preferably a sulfonic acid compound such as sulfuric acid, trifluoromethanesulfonic acid and p-toluenesulfonic acid. The catalyst is furthermore preferably a strong acid such as concentrated sulfuric acid and concentrated nitric acid, since the strong acid maintains the dehydration effect of an alkyl carbonate for a long time to promote the raction sufficiently with a small amount of the strong acid addition, and to save a treatment for removing the byproduct in the after process.

In the present invention, the amount of use of the catalyst is preferably as small as possible since the catalyst might possibly deteriorate the property of the silicone resin which is produced by using the recovered monomers and oligomers. The normal amount of use is 0.01% by weight or more based on the weight of the silicone compound.

In order to plymerize the decomposed monomers and oligomers produced from the silicone compound according to the present invention as a starting materials, a known technology, in which an alkoxysilane is hydrolyzed in the presence of a catalyst and is further condensated, can be utilized.

When dimethyl carbonate and methanol is used as alkyl carbonate and a compound containing active hydrogen group, respectively, the decomposition path of the silicone compound seems to be as follows in the process for recycling the silicone compounds according to the present invention: Dimethyl carbonate traps the water, which is produced by the decomposition reaction of the silicone compound and ceases the decomposition reaction, and decomposes into methanol and carbon dioxide, and contributes to the continuation of the decomposition reaction. The generated methanol contributes to further decomposition of silicone compound and the generated carbon dioxide is discharged from the reaction system.

The invention will now be described by the following examples that by no means limit the scope of the invention.

EXAMPLES

Ten grams (10 g) of commercially available silicone rubber was put into a flask having a reflux cooling tube, added was 10 g (0.11 mol) of dimethyl carbonate (reagent), 0.5 g (0.01 mol) of methanol and 20 mg (0.2 mmol) of sulfulic acid, and then the mixture was refluxed and stirred at 90° C. for 4 hours to decompose the silicone rubber. The reacted solution was obtained through a very mild reaction.

The decomposed product, the solid part (such as filler) of which was removed, was extracted using n-hexane, and was added with dimethyl chloride therein, then was analized by GC-MS method.

As a result, obtained decomposed products (about 200 kinds) were all siloxanes, which were monomers and oligomers, such as heptasiloxane. The decomposed products did not contain such as methoxy carbonate, for example, methyl formate which caused a deterioration in the property of the silicone rubber which was reproduced by using the recovered monomers and oligomers.

In above-mentioned example, since no byproduct was produced, saved were the time and the cost that might have been needed for the refining by separation. When compared with the conventional process, about 20% was saved in time according to the present invention. The yield of the process of the present invention was about 90%, but the remainder 10% seemed to be attributed to the loss in various steps in the process. Therefore, substantially 100% recycling efficiency seems to be possible according to the present invention.

The reacted solution, which was separately obtained according to the same process with the above-described process, was distilled to obtain dimethoxydimethylsilane. Ten grams (10 g) of the dimethoxydimethylsilane was put into a three-neck flask having a reflux cooling tube, then was added with 0.20 g of hexamethyldisiloxane and 150 ml of methanol as a reaction solvent. The mixture was added with 6.3 ml of water and 0.02 g of concentrated nitric acid under stirring at room temperature. After 20 minutes of stirring at room temperature, 0.01 g of di-n-butyltindilaurate was added as a condensation catalyst, then the mixture was further stirred for 3 hours at room temperature. The reaction system was subjected to decompressing with heating up to 120° C. under strong stirring, then the water containing methanol and hydrochloric acid was removed to obtain 6.1 g of polymethylhydrogensiloxane as a colorless transparent oil.

What is claimed is:

1. A process for recycling a silicone compound comprising the steps of:

(a) decomposing the silicone compound by employing an alkyl carbonate and a compound containing active hydrogen group in the presence of a catalyst; and (b) recovering silicone monomers and/or silicone oligomers from the decomposed silicone compound.

2. The process for recycling a silicone compound according to claim 1, wherein the catalyst is an acid catalyst.

3. The process for recycling a silicone compound according to claim 1, wherein the alkyl carbonate is a dimethyl carbonate.

4. The process for recycling a silicone compound according to claim 2, wherein the alkyl carbonate is a dimethyl carbonate.

5. The process for recycling a silicone compound according to claim 1, wherein the compound containing active hydrogen group is an alcohol.

* * * * *